United States Patent [19]

Benzie et al.

[11] 4,240,976

[45] * Dec. 23, 1980

[54] MANUFACTURE OF 3-PENTENE NITRILE

[75] Inventors: Robert J. Benzie; Dhafir Y. Waddan, both of Middlesbrough, England

[73] Assignee: Imperial Chemical Industries Limited, London, England

[*] Notice: The portion of the term of this patent subsequent to Oct. 28, 1997, has been disclaimed.

[21] Appl. No.: 24,550

[22] Filed: Mar. 28, 1979

Related U.S. Application Data

[63] Continuation of Ser. No. 874,225, Feb. 1, 1978, abandoned.

[30] Foreign Application Priority Data

Apr. 4, 1977 [GB] United Kingdom ............... 14064/77

[51] Int. Cl.$^3$ ........................................... C07C 120/02
[52] U.S. Cl. .................................................. 260/465.3
[58] Field of Search ...................................... 260/465.3

[56] References Cited

U.S. PATENT DOCUMENTS

| | | | |
|---|---|---|---|
| 3,711,527 | 1/1973 | Kurtz | 260/465.3 X |
| 3,869,501 | 3/1975 | Waddan | 260/465.3 |
| 4,048,216 | 9/1977 | Waddan | 260/465.3 |
| 4,096,171 | 6/1978 | Benzie et al. | 260/465.3 |

FOREIGN PATENT DOCUMENTS

| | | | |
|---|---|---|---|
| 1429169 | 3/1976 | United Kingdom | 260/465.3 |
| 1429651 | 3/1976 | United Kingdom | 260/465.3 |

*Primary Examiner*—Joseph Paul Brust
*Attorney, Agent, or Firm*—Cushman, Darby & Cushman

[57] ABSTRACT

A process for the manufacture of 3-pentene-nitrile is disclosed by reacting butadiene and hydrogen cyanide in the presence of a cuprous halide catalyst with an organic nitrile, the reactants present in specified proportions, the process being conducted in the presence of a further halide or mixtures of halides from an inorganic source of halide in addition to the amount from the cuprous halide.

9 Claims, No Drawings

MANUFACTURE OF 3-PENTENE NITRILE

This is a continuation, of application Ser. No. 874,225 filed Feb. 1, 1978, now abandoned.

This invention relates to the manufacture of organic nitriles and more particularly to their manufacture by reaction of olefinic compounds with hydrogen cyanide in the presence of a catalyst.

In British Pat. No. 1,429,651 there is described and claimed a process for the manufacture of organic nitriles which comprises reacting an olefin with hydrogen cyanide in the presence of a catalytic amount of a complex of a Group IB metal salt and an organic nitrile, the said complex being formed by mixing the said metal salt with the organic nitrile before or at the same time as it is mixed with the olefin and hydrogen cyanide. In the said prior process the use of complexes from cuprous chloride, cuprous bromide and cuprous iodide is said to be particularly important.

We have now found that when using complexes from cuprous chloride, bromide or iodide in the said process the catalytic activity is enhanced if there is present in the reaction medium chloride, bromide or iodide ion provided by an inorganic source of said halide ion and additional to that provided by the said cuprous halide.

Accordingly our invention provides a process for the manufacture of organic nitriles which comprises reacting an olefin with hydrogen cyanide in the presence of a catalytic amount of a complex of cuprous chloride, cuprous bromide or cuprous iodide with an organic nitrile, and in presence of chloride, bromide and/or iodide ion provided by an inorganic source of said halide ion and additional to that provided by the said cuprous halide, the said complex being formed by mixing the said cuprous halide with the organic nitrile before or at the same time as it is mixed with the olefin and hydrogen cyanide.

The cuprous chloride, bromide or iodide may be used singly or in admixture with one or both of the others in any relative proportions.

The organic nitrile which forms the complex with the said cuprous halide may contain one or more nitrile groups. Preferably the organic residue to which the nitrile groups are attached contains up to four carbon atoms. Such organic residues may be saturated or may contain ethylenic unsaturation. Particularly suitable organic nitriles for forming complexes with the said cuprous halide are acetonitrile, propionitrile, acrylonitrile, tetracyanoethylene, 3-pentenenitrile and adiponitrile.

The complexes of the organic nitrile with the said cuprous halide are formed by mixing the components, optionally in the presence of a solvent. It is important that the said cuprous halide is mixed with the organic nitrile before or at the same time as it is mixed with the olefin and the hydrogen cyanide. Both the olefin and the hydrogen cyanide will form a complex with the said cuprous halide and if this occurs before the introduction of the organic nitrile formation of the desired complex with the latter may be precluded. Thus, although organic nitriles are formed in the process of this invention, such nitriles, when formed after the initiation of the reaction, are not generally effective in promoting the catalytic effect of the said cuprous halide. For example, if 3-pentenenitrile is added to a said cuprous halide before or at the same time as the latter is added to butadiene and hydrogen cyanide to make 3-pentenenitrile an improved catalytic effect is obtained, but not otherwise.

The organic nitrile used to form the complex with the said cuprous halide may be used in approximately stoichiometric amount bearing in mind that each nitrile group of a compound containing more than one such group is capable of forming a complex with copper. Substantially more than the stoichiometric amount may be used, however, especially where the organic nitrile is capable of acting as a solvent, for example up to 100 times the stoichiometric amount.

The chloride, bromide and/or iodide ion additional to that provided by the said cuprous halide, is provided by an inorganic source of chloride, bromide and/or iodide ion other than the said cuprous halide. For example it may be provided by chlorine, bromine or iodine, by hydrogen chloride, hydrogen bromide or hydrogen iodide, by any inorganic chloride, bromide or iodide salt, especially alkali metal or alkaline earth metal salts, for example sodium chloride, bromide or iodide, potassium bromide, lithium bromide, magnesium bromide and calcium iodide. Mixtures of said chloride, bromide and iodide sources may of course be used. Lithium bromide is a preferred source of said halide ion.

The process of our invention may be carried out over a wide range of temperatures, for example from $-25°$ C. to $200°$ C., preferably from $20°$ to $150°$ C., and more preferably from $50°$ to $120°$ C. Owing to the volatility and toxicity of hydrogen cyanide the reaction is preferably conducted in a closed vessel under autogeneous pressure, or, if desired, under deliberately raised pressure, for example at a pressure of from 1 to 50 atmospheres. If desired a solvent may be used, for example a hydrocarbon solvent such as benzene, toluene or xylene, or a nitrile solvent such as acetonitrile, benzonitrile, 3-pentenenitrile or adiponitrile. Agitation of the reactants is desirable. The reaction is continued for a time sufficient to give a suitable conversion, for example from a few minutes, for example 5 minutes, up to a period of several days, for example 5 days.

The olefin and the hydrogen cyanide may be used in equimolar proportions or an excess of either may be used, especially within the molar range of olefin to hydrogen cyanide of 2:1 to 1:4. The complex of the said cuprous halide and the organic nitrile is used in catalytic amount; this will normally fall within the range 0.0005 to 0.1 moles of each per mole of olefin. We prefer that the proportion of the said complex is from 0.005 to 0.05 moles per mole of olefin.

The amount of chloride, bromide and/or iodide ion additional to that provided by the said cuprous halide may vary widely, for example it may be from 0.1 to 100 times the molar amount of halide provided by the said cuprous halide.

The organic nitrile formed in the process may be separated from the reaction mixture for example by first removing any excess olefin and/or hydrogen cyanide by distillation or by simply venting the apparatus. The organic nitrile may then be separated from catalyst residues by conventional methods such as filtration with or without extraction with solvent, or by distillation. The process may readily be adapted to continuous operation.

The process of our invention is particularly valuable for the conversion of butadiene to 3-pentene nitrile.

3-Pentenenitrile is particularly valuable for further reaction with hydrogen cyanide in the presence of a catalyst to give adiponitrile. Adiponitrile may be hydrogenated to hexamethylene diamine, a valuable intermediate for polycondensation with dicarboxylic acids to give polyamides, especially, for example, with adipic acid to give polyhexamethylene adipamide (nylon 6,6) a well-known polyamide for use in the manufacture of mouldings and for melt spinning into synthetic fibres.

The use of chloride, bromide and/or iodide ion provided by an inorganic source of said halide ion and in addition to that provided by the said cuprous halide leads to enhanced catalyst activity manifest in increased conversion at limited reaction times.

The invention is illustrated but not limited by the following Example.

EXAMPLES

Cuprous bromide (6 g, 0.042 mole) and the additive listed in the following Table were added to 20 ml of adiponitrile, the mixture warmed to 60° C. to give complete solution which was then cooled and charged to a pressure reactor. After purging with nitrogen, butadiene (100 ml, 62 g, 1.15 mole) and hydrogen cyanide (50 ml, 34.4 g, 1.27 mole) were charged to the reactor which was heated until the internal temperature reached 120° C. (in approximately 1 hour) and then maintained at this temperature for the time specified in the following Table. The low-boiling material was then distilled off from the adiponitrile and catalyst, and the 3-pentenenitrile product in the distillate estimated by gas-liquid chromatography. The percentage conversion of butadiene to 3-pentenenitrile for various times of reaction is shown in the following Table.

| Additive | Amount | % Butadiene Converted Reaction Time | | |
|---|---|---|---|---|
| | | 2 hours | 5 hours | 10 hours |
| None | — | 40 | 58 | 87 |
| Hydrobromic acid | 0.25g. | 51 | 77 | — |
| Potassium bromide | 1.0g. | — | 67 | — |
| Lithium bromide | 1.0g. | 73 | 75 | 92 |
| Iodine | 0.5g. | — | 77 | — |
| Sodium Iodide | 0.5g. | — | 83 | — |

We claim:

1. In a process for the manufacture of 3-pentenenitrile which process comprises reacting at a temperature within the range −25° C. to 200° C. a mixture of butadiene and hydrogen cyanide which is substantially completely devoid of oxygen and in the presence as catalyst of a cuprous halide complex selected from the group consisting of cuprous chloride, cuprous bromide or cuprous iodide with an organic nitrile, the catalyst being used in a catalytic amount of 0.0005 to 0.1 mole per mole of butadiene, the molar ratio of butadiene to hydrogen cyanide being 2:1 to 1:4 and the catalyst complex being formed by mixing the said cuprous halide with the said organic nitrile before or at the same time as it is mixed with the butadiene and hydrogen cyanide, the improvement wherein the process is carried out in the presence of further chloride ion, bromide ion, iodide ion or mixtures thereof provided by an inorganic source of halide ion additional to said catalytic amount of cuprous halide.

2. The process of claim 1 in which the inorganic source of said halide ion is selected from chlorine, bromine, iodine, hydrogen chloride, hydrogen bromide, hydrogen iodide and inorganic chloride, bromide and iodide salts.

3. The process of claim 2 in which the inorganic chloride, bromide or iodide salt is an alkali metal or alkaline earth metal salt.

4. The process of claim 3 in which the alkali metal salt is lithium bromide.

5. The process of claim 1 in which the amount of chloride, bromide and/or iodide ion additional to that provided by the said cuprous halide is from 0.1 to 100 times the molar amount of halide provided by the said cuprous halide.

6. The process of claim 1 in which the organic residue to which the nitrile groups are attached in the organic nitrile which forms the complex with the said cuprous halide contains up to four carbon atoms.

7. The process of claim 1 in which the organic nitrile which forms the complex with the said cuprous halide is selected from acetonitrile, propionitrile, acrylonitrile, tetracyanoethylene, 3-pentenenitrile and adiponitrile.

8. The process of claim 1 in which the organic nitrile which forms the complex with the said cuprous halide is used in from 1 to 100 times the stoichiometric amount in relation to the said cuprous halide.

9. In a process for the manufacture of 3-pentenenitrile which comprises reacting at a temperature of −25° C. to 200° C. a mixture of butadiene and hydrogen cyanide which is substantially completely devoid of oxygen and in the presence as catalyst of a complex of cuprous chloride, cuprous bromide or cuprous iodide with an organic nitrile, the catalyst being used in a catalytic amount of 0.0005 to 0.1 mole per mole of butadiene, the molar ratio of butadiene to hydrogen cyanide being 2:1 to 1:4 and the catalyst complex being formed by mixing the cuprous halide with the organic nitrile before or at the same time as the catalyst is mixed with the butadiene and hydrogen cyanide, the improvement of conducting the process in the presence of further chloride ion, bromide ion, iodide ion or mixtures thereof additional to said catalytic amount of said cuprous halide, which ions are provided by an inorganic source of halide ion selected from the group consisting of chlorine, bromine, iodine, hydrogen chloride, hydrogen bromine, hydrogen iodide and inorganic chloride, bromide and iodine salts and in an amount of from about 0.1 to about 100 times the molar amount of halide provided by the cuprous halide, wherein the organic residue to which the nitrile groups are attached in the organic nitrile which forms the complex with said cuprous halide contains up to four carbon atoms.

* * * * *